United States Patent
Hu

(10) Patent No.: US 8,694,121 B2
(45) Date of Patent: Apr. 8, 2014

(54) PROGRAMMABLE SWITCHING CIRCUIT WITH CHARGE PUMPS FOR BIO-STIMULATOR

(75) Inventor: Weichih Hu, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 2038 days.

(21) Appl. No.: 11/443,044

(22) Filed: May 31, 2006

(65) Prior Publication Data

US 2007/0282399 A1    Dec. 6, 2007

(51) Int. Cl.
*A61N 1/02* (2006.01)
(52) U.S. Cl.
USPC .......................................................... 607/70
(58) Field of Classification Search
USPC .......................................................... 607/70
See application file for complete search history.

(56) References Cited

U.S. PATENT DOCUMENTS 6,106,551 A * 8/2000 Crossett et al. ............... 623/3.28
2005/0075677 A1* 4/2005 Ganion et al. ..................... 607/9

* cited by examiner

*Primary Examiner* — Eric D. Bertram
(74) *Attorney, Agent, or Firm* — WPAT, PC; Justin King

(57) ABSTRACT

A programmable switching circuit with charge pumps for a bio-stimulator is disclosed. A programmable controlling circuit generates a set of binary bits according to a controlling program and then uses a universal asynchronous receiver/transmitter for outputting to the pulse signal generating circuit so as to generate two pulse signals with the predetermined waveforms and different phases. Then, according to these two pulse signals with different phases, two charge pumps included in a charge pump regulating circuit output currents with specific voltage intensity through two output routes. The amplitude of the current is determined by the capacitor on each output route. Additionally, the programmable controlling circuit determines which route to be outputted so as to control and switch the polarities and current amplitude of a bio-stimulator.

13 Claims, 2 Drawing Sheets

PROGRAMMABLE SWITCHING CIRCUIT WITH CHARGE PUMPS FOR BIO-STIMULATOR

BACKGROUND OF THE INVENTION

1. Field of the Invention

The present invention is generally related to a discharge circuit of an electronic stimulator and more particularly to a discharge circuit of a programmable exciting switching circuit with charge pumps.

2. Description of the Prior Art

The technology of the stimulator devices includes two major categories, one utilizing a transformer as the output element and the other one utilizing a capacitor storing electric charges and then generating an electric output pulse by instant discharge as the output element.

The above two types of output devices both utilize passive elements as the output elements. In the output method of current and voltage, the stimulator device using a transformer as the output element utilizes the analog output method to raise the voltage instantly by the transformer and adjusts its output current and voltage by dividing current in analog circuitry applicable to the stimulator device with larger current amplitude and continuous stimuli. On the other hand, the stimulator device using a capacitor to store electric charges and then discharge instantly utilizes the charging time of the capacitor to control its output current and voltage. By this method, the output of the current and voltage is a bit harder to control. However, it has the advantage of applying in portable or compact stimulator devices for smaller output current amplitude.

In the application of the electronic stimulator, the direction of the discharge needs to be changed or the current amplitude needs to be adjusted dynamically. For instance, the stimulator generally uses two patches as the two discharge electrodes and these two electrodes may be expected to alternating discharge. The period and the intensity of the discharge may need to be altered, such as the intensity of the discharge gradually increases or decreases, or the like.

In order to fulfill the above described requirements, the control of the current or voltage needs to be flexible. Due to the difficulty in specifically controlling the output current and voltage for the stimulator using either a transformer as the output element or a capacitor storing electric charges and discharging instantly, an improved design is required to effectively control the current and voltage, especially for a portable device.

SUMMARY OF THE INVENTION

In accordance with the present invention, a programmable switching circuit with charge pumps for bio-stimulator is provided. The programmable switching circuit with charge pumps for bio-stimulator of the invention meets the above described requirements that cannot be satisfied by a conventional one.

One object of the present invention is to provide a programmable switching circuit with charge pumps for bio-stimulator comprising a programmable controlling circuit, a pulse signal generating circuit, a charge pump regulating circuit, and a selection controlling circuit. The programmable controlling circuit generates a set of binary bits according to a controlling program and then uses a universal asynchronous receiver/transmitter for outputting to the pulse signal generating circuit so as to generate two pulse signals with the predetermined waveforms and different phases. Then, according to these two pulse signals with different phases, the two charge pumps included in the charge pump regulating circuit output currents with the specific voltage intensity through two output routes. The amplitude of the current is determined by the capacitor on each output route. Additionally, the programmable controlling circuit determines which route to be outputted so as to achieve the switching function.

DESCRIPTION OF THE PREFERRED EMBODIMENTS

What is probed into the invention is a programmable switching circuit with charge pumps for bio-stimulator. Detail descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In order to effectively control the current and voltage of an output element so as to output continuously, the bio-stimulator has to generate and then output a constant current with an arbitrary waveform and any intensity of the voltage. Therefore, the present invention utilizes the principle of exciting a switching charge pump by an oscillation circuit whose excitation clock controls the intensity of the voltage. The application of exciting a switching charge pump is provided mainly for regulating the voltage of the applied circuit and transforming the specific input voltage into the required output voltage. Besides, an external capacitor is used to provide stable current output to match with the oscillation circuit and the clock so as to increase the output voltage.

Figure 1:
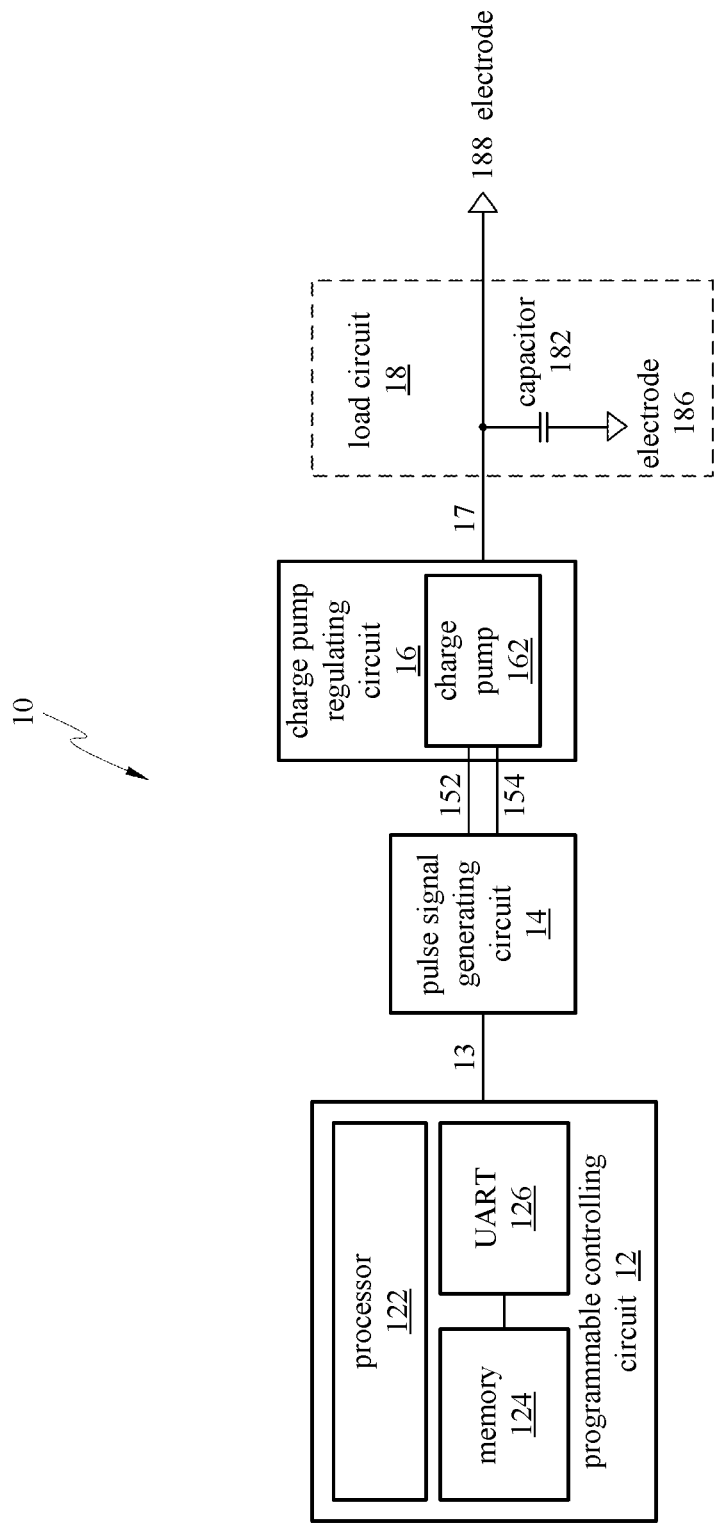
FIG. 1 is a schematic functional block diagram of an embodiment of the present invention; and, FIG. 2 is a schematic functional block diagram of another embodiment of the present invention.

As shown in FIG. 1, an embodiment of the invention discloses a programmable switching circuit with charge pumps for bio-stimulator 10 comprising a programmable controlling circuit 12, a pulse signal generating circuit 14, a charge pump regulating circuit 16, and a load circuit 18. According to a controlling program, the programmable controlling circuit 12 generates a pulse controlling signal transmitted to the pulse signal generating circuit 14 through a circuit path 13. According to the pulse controlling signal, the pulse signal generating circuit 14 generates a first pulse signal and a second pulse signal that are transmitted to the charge pump regulating circuit 16 through a circuit path 15. According to the first and the second pulse signals, the charge pump regulating circuit 16 generates an output signal transmitted to the load circuit 18 through a circuit path 17 and outputted by the load circuit.

The programmable controlling circuit 12 includes a processor 122, a memory 124, and a universal asynchronous receiver/transmitter (UART) 126. The memory 124 stores the controlling program that includes a plurality of sets of numbers. Thus, the processor 122 provides a set of numbers from the memory 124 to the UART 126 at a time. The UART 126 outputs sequential signals according to these numbers. Different numbers generate different waveforms for output. For example, each set of numbers are stored in one byte of the memory 124 in binary form. One byte can be 2 bits, 4 bits, 8 bits, 16 bits, 32 bits, or other possible number of bits. 0 or 1 of each bit represents the low or high potential of the output signal from the UART 126. Therefore, by a series of binary bits representing a binary number, the UART 126 can provide a series of continuous outputs with high and low potentials so as to generate specific waveforms.

According to the waveforms transmitted by the circuit path 13, the pulse signal generating circuit 14 generates a first pulse signal and a second pulse signal that are then transmitted through circuit paths 152 and 154 of the circuit path 15, respectively. The first pulse signal and the second pulse signal can be outputted with different phases. The phase difference of the first pulse signal and the second pulse signal can be 90, 180, 270 degrees or any proper number that is not limited in the present invention.

It is known technique that a charge pump together with two different pulse signals can transform an input voltage to a predetermined intensity of the voltage. According to the above technique, in an embodiment of the invention the charge pump regulating circuit 16 includes a charge pump 162 that transforms an input voltage to an output signal with a predetermined intensity of the voltage in accord with its waveform and the pulse controlling signal. For example, the waveform of the output signal has the same cycle as the pulse controlling signal but different electric potential from the pulse controlling signal.

The load circuit 18 includes a capacitor 182 connecting two electrodes 186 and 188. The capacitor 182 determines the amplitude of the released current. The electrodes 186 and 188 can be connected with two patches. By attaching the patch to human being, the output signal is outputted to the human being.

Figure 2:
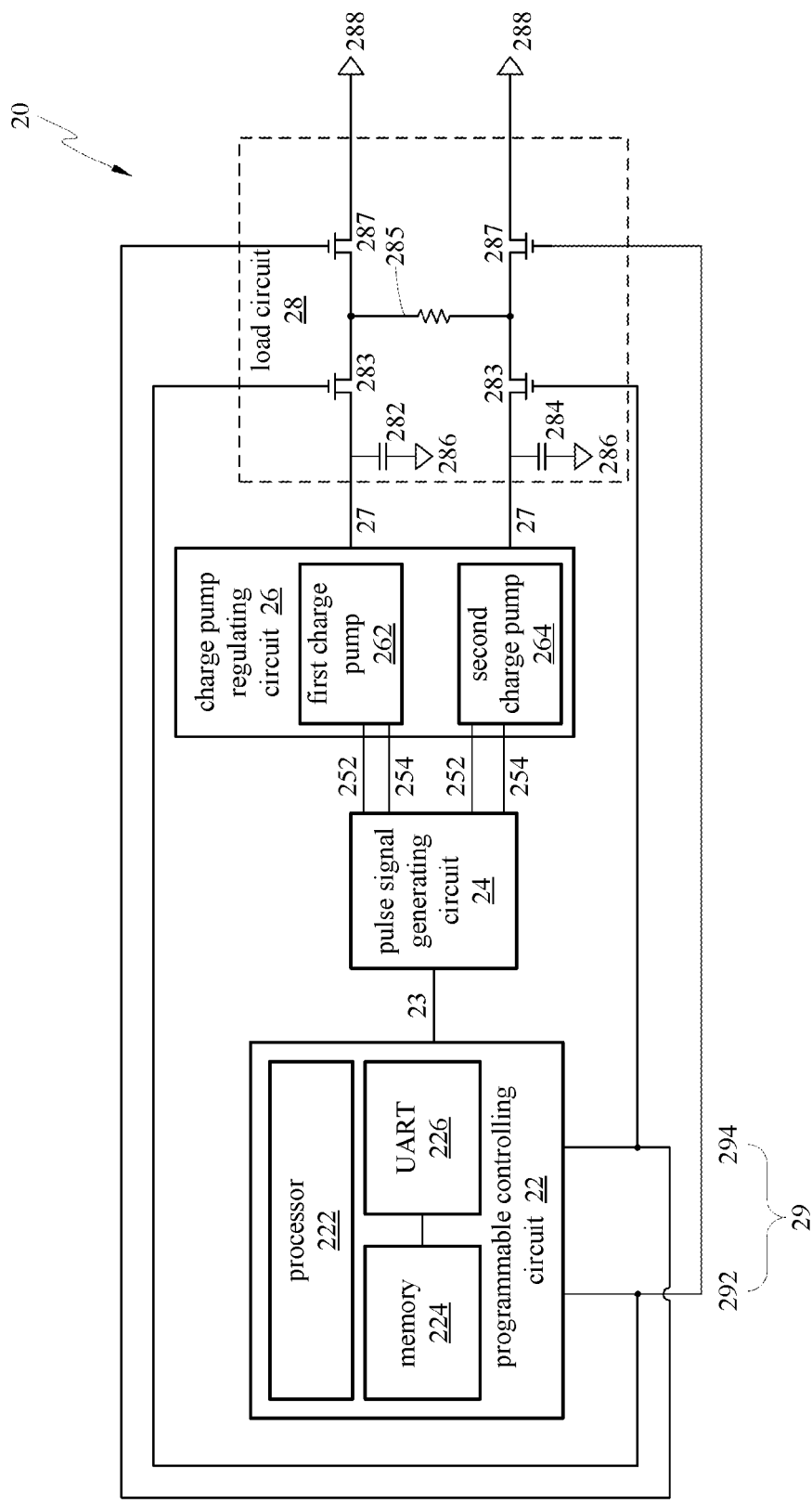

In order to obtain the stimulus of an alternating electric energy, two sets of exciting switching circuit with charge pumps are required to control the circuit to select an output. Therefore, as shown in FIG. 2, another embodiment of the invention discloses a programmable switching circuit with charge pumps for bio-stimulator 22 comprising a programmable controlling circuit 22, a pulse signal generating circuit 24, a charge pump regulating circuit 26, and a selection controlling circuit 28. According to a controlling program, the programmable controlling circuit 22 generates a pulse controlling signal and a selection controlling signal. The pulse controlling signal is transmitted to the pulse signal generating circuit 24 through a circuit path 23. According to the pulse controlling signal, the pulse signal generating circuit 24 generates a first pulse signal and a second pulse signal that are transmitted to the charge pump regulating circuit 26 through a circuit path 25. According to the first and the second pulse signals, the charge pump regulating circuit 26 generates a first output signal and a second output signal that are transmitted to the selection controlling circuit 28 through a circuit path 27. The selection controlling circuit 28 includes a first route and a second route for transmitting the first output signal and the second output signal, respectively. The selection controlling signal transmitted by the circuit path 29 selects either the first route or the second route.

The programmable controlling circuit 22 has the same function as the programmable controlling circuit 12 shown in FIG. 1, outputting a pulse controlling signal to the pulse signal generating circuit 24 through the circuit path 23. Additionally, the programmable controlling circuit 22 generates a selection controlling signal transmitted to the selection controlling circuit 28 through the circuit path 29.

The pulse signal generating circuit 24 has the same function as the pulse signal generating circuit 14 shown in FIG. 1. According to the waveforms transmitted by the circuit path 23, the pulse signal generating circuit 14 generates a first pulse signal and a second pulse signal that are then transmitted through circuit paths 252 and 254 of the circuit path 25, respectively.

The charge pump regulating circuit 26 includes a first charge pump 262 and a second charge pump 264. The first charge pump 262 and the second charge pump 264 have the same function as the charge pump 162 shown in FIG. 1. The charge pumps transform an input voltage to a first and a second output signals with a predetermined intensity of the voltage. The waveforms of the first and the second output signals are generated according to the waveforms of the first and the second pulse signals, respectively. The circuit paths 252 and 254 become the input of the first charge pump 262 and the second charge pump 264 corresponding to the charge pump regulating circuit 26.

According to the selection controlling signal, the selection controlling circuit 28 selects either the first output signal or the second output signal for output. Thus, in the embodiment of the invention the selection controlling circuit 28 includes a first route and a second route for outputting the first output signal and the second output signal, respectively, wherein the first route and the second route share a common route 285. The first route and the second route each include a first switch 283 and a second switch 287 at the two ends of the common route 285. A resistor can be provided in the common route 285. Besides, the first route and the second route have capacitors 282 and 284, respectively. The capacitors 282 and 284 determine the current amplitudes of the first output signal and the second output signal, respectively.

The first output signal and the second output signal each are sequentially transmitted through the first switch 283, the common route 285, and the second switch 287. The two ends of the capacitors 282 and 284 are a first contact provided between the charge pump regulating circuit and the first switch 283, and a second contact connected to a first electrode 286. Furthermore, the two ends of the second switch 287 are connected to the common route 285 and a second electrode 288, respectively. The first electrode 286 and the second electrode 288 have the same function as the first electrode 186 and the second electrode 188 shown in FIG. 1. In an embodiment of the invention the first electrode 286 of the first route together with the second electrode 288 of the second route are connected to the same patch while the second electrode 288 of the first route together with the first electrode 286 of the second route are connected to the same patch.

In order to select an output from the first route and the second route, the selection controlling signal has to select a set of the switches 283 and 287 to open and a set of those to close from the two sets of the first switch 283 and the second switch 287. The selection controlling signal includes a first selection controlling signal and a second selection controlling signal that have opposite electric properties. The first selection controlling signal controls the first switch 283 of the first route and the second switch 287 of the second route while the second selection controlling signal controls the second switch 287 of the first route and the first switch 283 of the second route.

Thus, the first selection controlling signal and the second selection controlling signal are outputted by the circuit paths 292 and 294 of the circuit path 29. The circuit path 292 is connected to the first switch 283 of the first route and the second switch 287 of the second route while the circuit path 294 is connected to the second switch 287 of the first route and the first switch 283 of the second route.

It is obvious for those who skilled in the art that the discharge pump used in the present invention is not limited to one or two and can be three or more than three. Therefore, in an embodiment of the invention the charge pump regulating circuit can include a plurality of charge pumps to generate a plurality of output signals according to the first pulse signal and the second pulse signal. The selection controlling circuit selects an output from a plurality of output signals by a multiplexer according to the selection controlling signal.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A programmable switching circuit with charge pumps for bio-stimulator, comprising:
   a programmable controlling circuit generating a pulse controlling signal and a selection controlling signal according to a controlling program;
   a pulse signal generating circuit generating a first pulse signal and a second pulse signal according to the pulse controlling signal, wherein the phase difference of the first pulse signal and the second pulse signal is 180 degrees to provide an alternative current;
   a charge pump regulating circuit including a first charge pump and a second charge pump, wherein said first and said second charge pumps generate a first and a second output signals, respectively, according to the first and the second pulse signals; and
   a selection controlling circuit selecting either the first output signal outputted by a first route or the second output signal outputted by a second route according to the selection controlling signal to provide said alternative current, said first and said second routes that share a common route and individually include a first switch and a second switch at the two ends of said common route.

2. The programmable switching circuit with charge pumps for bio-stimulator according to claim 1, wherein said programmable controlling circuit includes a memory for storing said controlling program.

3. The programmable switching circuit with charge pumps for bio-stimulator according to claim 1, wherein said programmable controlling circuit includes a universal asynchronous receiver/transmitter to generate the waveform for the pulse controlling signal.

4. The programmable switching circuit with charge pumps for bio-stimulator according to claim 3, wherein the controlling program includes plurality sets of numbers for said universal asynchronous receiver/transmitter to generate the waveform for the pulse controlling signal.

5. The programmable switching circuit with charge pumps for bio-stimulator according to claim 1, wherein said pulse signal generating circuit generates the first and the second pulse signals according to the waveform of the pulse controlling signal.

6. The programmable switching circuit with charge pumps for bio-stimulator according to claim 1, wherein the waveforms of the first output signal and the second output signal are generated according to the waveforms of the first and the second pulse signals, respectively.

7. The programmable switching circuit with charge pumps for bio-stimulator according to claim 1, wherein the selection controlling signal includes a first selection signal, controlling said first switch of said first route and said second switch of said second route, and a second selection signal, controlling said second switch of said first route and said first switch of said second route.

8. The programmable switching circuit with charge pumps for bio-stimulator according to claim 7, wherein the electric properties of the first and the second selection controlling signals are opposite to each other.

9. The programmable switching circuit with charge pumps for bio-stimulator according to claim 7, wherein the first output signal and the second output signal are sequentially transmitted through said first switch, said common route, and said second switch, respectively.

10. The programmable switching circuit with charge pumps for bio-stimulator according to claim 1, wherein said first route and said second route each include a capacitor and said capacitors of said first route and said second route determine the current amplitude of the first and the second output signals, respectively.

11. The programmable switching circuit with charge pumps for bio-stimulator according to claim 10, wherein the two ends of said capacitors are a first contact provided between said charge pump regulating circuit and said first switch, and a second contact connected to a first electrode.

12. The programmable switching circuit with charge pumps for bio-stimulator according to claim 11, wherein the two ends of said second switch are connected with said common route and second electrode, respectively.

13. The programmable switching circuit with charge pumps for bio-stimulator according to claim 1, wherein said common route includes a resistor.

* * * * *